United States Patent [19]
Webster

[11] Patent Number: 5,684,218
[45] Date of Patent: Nov. 4, 1997

[54] PREPARATION OF TETRAFLUOROETHYLENE

[75] Inventor: James Lang Webster, Parkersburg, W. Va.

[73] Assignee: E. I. Du Pont de Nemours and Company, Wilmington, Del.

[21] Appl. No.: 621,551

[22] Filed: Mar. 25, 1996

Related U.S. Application Data

[63] Continuation-in-part of Ser. No. 414,967, Mar. 31, 1995, abandoned.

[51] Int. Cl.$^6$ ........................... C07C 51/14
[52] U.S. Cl. ........................... 570/150
[58] Field of Search ........................... 570/150

[56] References Cited

U.S. PATENT DOCUMENTS 2,835,711  5/1958  Wolfe et al. .
2,941,012  4/1960  Forshey .

Primary Examiner—Samuel Barts

[57] ABSTRACT

Tetrafluoroethylene is obtained by subjecting metal fluoride, such as sodium fluoride, calcium fluoride or silicon fluoride, to a plasma to form a gaseous mixture of metal and reactive fluorine. This gaseous mixture is then reacted with a bed of carbon particles at a temperature at which the metal, when non-carbonaceous, does not condense. The resultant reaction mixture is then quenched to obtain the tetrafluoroethylene. Typically, the plasma will be at a temperature of at least 4500° C. and the temperature of the carbon bed will be in the range of 2000° C. to 3500° C.

27 Claims, 1 Drawing Sheet

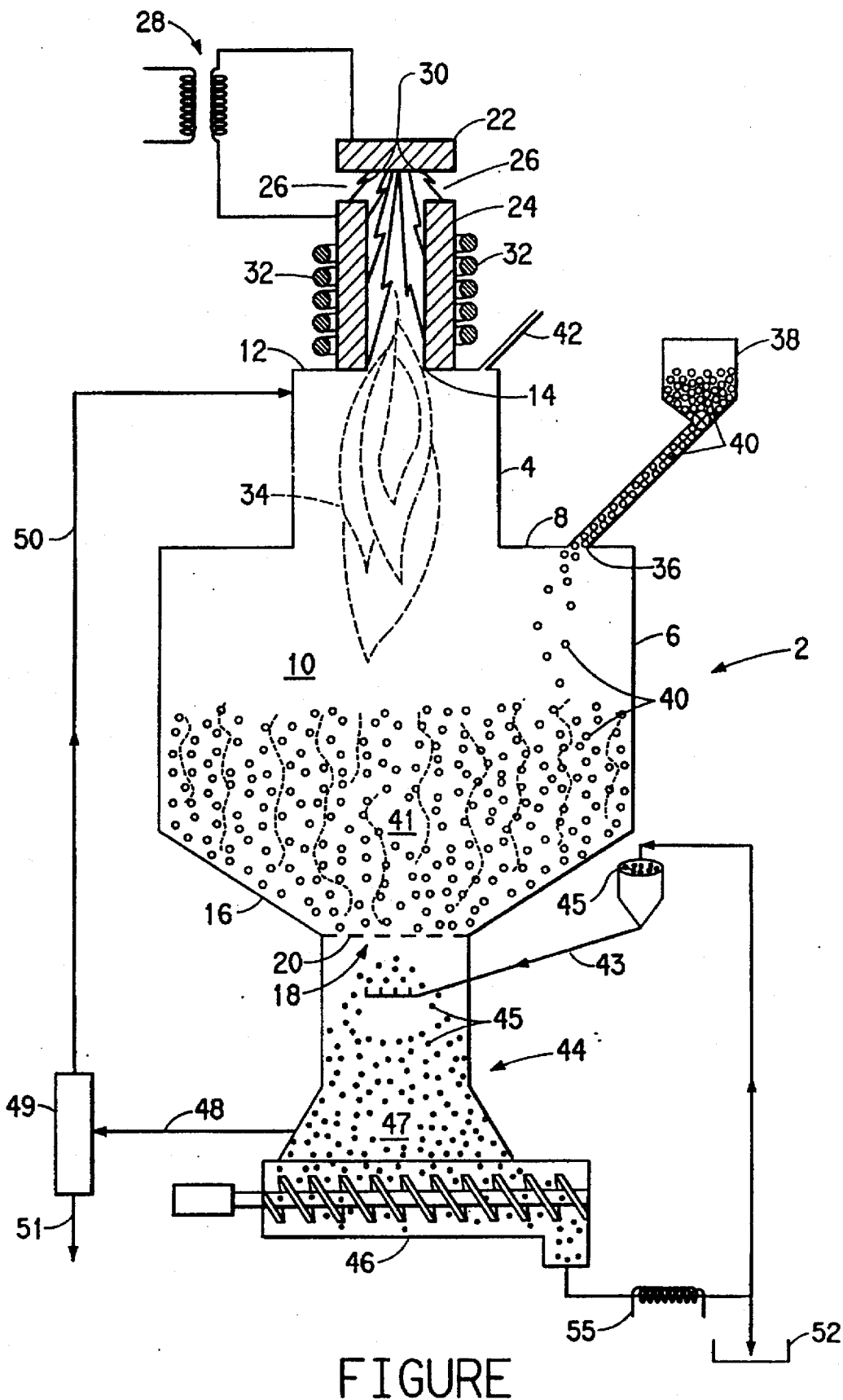
FIGURE

5,684,218

1

PREPARATION OF TETRAFLUOROETHYLENE

CROSS REFERENCE TO RELATED APPLICATIONS

This Application is a Continuation-In-Part of Application Ser. No. 08/414,967, filed Mar. 31, 1995, by the same inventor, now abandoned.

FIELD OF THE INVENTION

This invention relates to a process for the preparation of tetrafluoroethylene without using $CHClF_2$ as starting material.

BACKGROUND OF THE INVENTION

U.S. Pat. No. 2,835,711 (Wolfe et al.) discloses a batch process for reacting fluorides of Group IIA elements of the Periodic Table with carbon to form fluorocarbons which have a variety of utilities, including as intermediates for conversion to tetrafluoroethylene. Only details for high melting Group IIA metal fluorides are given and these involve the melting of the metal fluoride in a crucible by using a carbon arc. Powdered carbon can also be mixed with the metal fluoride in the crucible and the carbon electrodes immersed in the resultant mixture. Gaseous fluorocarbons, primarily $CF_4$, evolve from the resultant melt, leaving behind the reaction product between the metal of the metal fluoride and carbon, which is identified as $CaC_2$ in Example 1.

U.S. Pat. No. 2,709,191 (Farlow et al.) discloses the reaction of silicon fluoride with carbon to produce tetrafluoroethylene at extremely low conversions of the silicon fluoride per pass (Example II) and obtaining increasing proportions of $CF_4$ instead of tetrafluoroethylene at multiple passes (Example I). The "pass" in the process is the passage of silicon fluoride gas at a slow rate through the burning arc struck between two graphite electrodes, and then the gas (reaction product and unreacted silicon fluoride) flows through the hollow bore of one of the electrodes. The carbon reactant of the process comes from consumable carbon electrode, although carbon powder can also be flowed through the arc with the silicon fluoride. Various operating pressures are disclosed but low pressure (1 to 150 mm of mercury) is disclosed to be preferable to decrease the difficulty of the operation of the arc. Argon can be used to set the operating pressure, which is then maintained by the silicon fluoride feed. The gaseous reaction mixture is quenched to a temperature no higher than 400° C. within 0.001 to 0.1 sec.

U.S. Pat. No. 3,081,245 (Farlow) discloses an improved arc process for synthesizing tetrafluorothylene, in which saturated fluorocarbon is the feed material to the arc. After passage through the arc, the resultant gaseous reaction product is passed through a carbon bed at a temperature of 2000° to 2700° C. and then quenched. Conversion of the saturated fluorocarbon is quite low, reported as being less than 15% in Table 1.

The Farlow processes have never achieved commercial exploitation for the manufacture of tetrafluoroethylene (TFE) because of the low conversion and/or low yield giving a generally low production rate of this product. Instead, TFE has been made commercially worldwide by an entirely different process since the 1950's by a series of process steps, involving (i) reaction of $CaF_2$ with $H_2SO_4$ to form HF, (ii) synthesis of chloroform, (iii) reaction of HF with chloroform to form chlorodifluoromethane (HCFC-22), and (iv) pyrolysis of HCFC-22 to form TFE, and refining the TFE. This series of processes starts with a reactant used in the Wolfe process, but then proceeds on a journey involving the building of four plants ((i) to (iv) above) to arrive at the reaction product of the Farlow process at a high production rate, nevertheless making the manufacture of TFE very expensive, and creating a large amount of HCl byproduct for further processing or disposal.

There has existed a long-felt need for the ability to produce tetrafluoroethylene more economically.

SUMMARY OF THE INVENTION

The present invention satisfies this need by the process for the manufacture of tetrafluoroethylene comprising subjecting non-carbonceous metal fluoride to a plasma to cause the metal fluoride to dissociate into a gaseous mixture of metal and reactive fluorine, flowing the gaseous mixture into intimate contact with particulate carbon at a temperature which is greater than the temperature at which the metal, in the gaseous mixture condenses, whereby said reactive fluorine and said carbon react with one another to form a gaseous precursor to tetrafluoroethylene, and quenching said gaseous precursor to obtain gaseous tetrafluoroethylene.

Another embodiment of the present invention is apparatus useful for carrying out the process, comprising means for defining a reaction chamber, means for forming a plasma at one end of said reaction chamber, means for containing particulate reactant at the opposite end of said reactive chamber, means for flowing gas into and through said plasma to cause it to extend unconfined into said reaction chamber and directed towards said opposite end of said chamber, said chamber containing means including perforate means for supporting said particulate reactant while permitting said flowing gas to pass therethrough, and means for receiving said flowing gas after passage through said perforate means for quenching said gas.

In one aspect of this embodiment, the flowing gas is a co-reactant for said particulate reactant. In another aspect, additional means are provided to feed the co-reactant into said plasma.

BRIEF DESCRIPTION OF THE DRAWINGS

The Figure shows in schematic cross-sectional side elevation, one embodiment of apparatus of the present invention.

DETAILED DESCRIPTION

The apparatus of the Figure will be first described, as an aid to understanding the process of the present invention.

The chemical reactor 2 in the embodiment of the Figure is formed from a pair of stacked cylindrical structures 4 and 6 of increasing diameter interconnected via apron 8 and having their interiors in communication with one another to form a reaction chamber 10. The ends of the reaction chamber 10 are formed from a closure plate 12 sealing the top of cylinder structure 4, except for central opening 14 therein and an inwardly tapering (conical) wall 16 joining the bottom of cylindrical structure 6 and defining a bottom opening 18 in the reaction chamber. A perforated plate 20 bridges this opening. The opening 14 forms an inlet to the reaction chamber and the opening 18 forms the outlet to the reaction chamber at its opposite end.

Positioned about the opening 14 are cylindrical electrodes 22 and 24 of opposite polarity and separated by space 26. An electrical power source such as transformer 28 supplies electrical energy with sufficient voltage and current to create and sustain arc 30 struck between the electrodes. A gas is fed under pressure by means such as a blower (not shown) into this arc via the space 26 and is directed into the reaction chamber 10. This flow of the gas through the arc forms a plasma of the gas extending from the arc 30 into the hollow bore of electrode 24, and because the temperature of the arc is thousands of degrees centigrade, the plasma can be considered to be a thermal plasma. The cylindrical electrode 22 may also have a hollow bore (not shown) for feeding gas in the direction of the reaction chamber 10 to direct the overall gas flow into the reaction chamber. This directionality of the gas flow can also be accomplished by feeding the gas through space 26 from multiple locations around the outer periphery of the electrodes. The flow of the gas into the reaction chamber 10 extends this plasma into the chamber.

The portion of the plasma extending into the chamber is shown in the drawing as a plume or flame 34, which is luminous so as to be visible to the eye. The flame is not confined to the hollow bore of the electrode 24. The exterior of the flame into the cylindrical structure 4 is preferably a free flame in that it is undefined by either structure 4 or 6. Normally, the cylindrical structure 4 will be of heat resistant material, such as graphite, and will be cooled. Since the flame extends beyond electrode 24, the flame is essentially free of electric current flowing directly between electrodes 22 and 24. The flame, however, may have a small electrical charge resulting from dissociated gas. The flame is preferably rotated by magnetic coil 32 encircling electrode 24; this rotation helps cause turbulence within the plasma and helps protect the electrodes from erosion. This turbulence extends into the flame to promote intermixing of the feed material fed into the flame.

An opening 36 is provided in apron 8 to permit feeding means 38 to add particulate reactant 40 (reactant particles) to the bottom of the reaction chamber, resting on the tapering wall 16 and perforated plate 20, both of which are also made of thermally resistant material such as graphite. The reactant particles 40 are shown being fed to the reaction chamber and forming a bed 41 thereof at its bottom. Multiple feeding means 38 can be used spaced around apron 8 (and around electrode 24) in order to supply particles 40 over the entire bed 41.

The flowing gas which forms the plasma flame 34 is directed at the outlet of the reaction chamber, to pass into and through the bed 4 of reactant particles and then through perforated plate 20 in an essentially straight line overall path, i.e., the gas may whirl about in the flame and will change direction when passing through bed 41, but will nevertheless essentially always be heading for the plate 20.

Co-reactant for the reactant particles 40 is also supplied to the reaction chamber 10. The flowing gas is either the co-reactant or is a gas other than co-reactant, such as an inert gas. In either case, the gas dissociates in the arc 30 and it is the dissociated species which forms the plasma and its flame 34.

When the flowing gas is not co-reactant, an inlet line 42 in closure plate 12 is provided for feeding the co-reactant into the plasma flame 34 for dissociation therein. In this embodiment, the co-reactant does not come into contact with the electrodes, which may save them from corrosion by the co-reactant. Multiple inlet lines 42 spaced around closure plate 12 can be used. The feed of metal fluoride into the plasma flame can be at high velocity, such as sonic velocity, (maximum flow) to insure that the metal fluoride enteres into the interior, i.e. the hottest portion of the plasma flame.

A quenching chamber 44 is positioned at the outlet end of the reaction chamber to receive the flow of gas through the perforated plate 20. Within the quenching chamber in the embodiment shown are cool quenching particles 45, fed via inlet line 43 as a spray shower directed countercurrent to the flow of gas from chamber 10, with the particles 45 then settling to form a bed 47 thereof, which instantly cools the hot gas from the plasma. The quenching particles are continuously removed at the bottom of the quenching chamber 44 via auger 46 for cooling by cooler 55 and recycling to this chamber via inlet line 43. The cooled gas exits the quenching chamber 44 via line 48 where it is subjected to further cooling and separation of desired and undesired product, such as by distillation 49, with the undesired product being recycled to the reaction chamber 10 via line 50 and the desired product, TFE, being obtained via line 51. Multiple lines 50 spaced diametrically around the cylinder structure 4 and aiming into the flame 34 can be used.

From this apparatus arrangement, it can be seen that the reaction chamber will contain two reaction zones contiguous to one another and the inlet 14 and outlet 18 are oppositely disposed to one another. In the first zone, one reactant is thermally dissociated in the plasma and in the second zone the reaction between the resultant reactive species from the plasma and the bed of reactant particles occurs. The reactor 2 is preferably positioned so that the gas flow is vertically downward, although the reactor 2 can be disposed differently so as to provide a different direction of gas flow, and the reactor chamber 10 can have many different configurations. In the vertical disposition, any solids that are present in the reaction chamber above the bed 41 of reactant particles, e.g., undissociated co-reactant or solid reaction products simply fall by gravity onto the bed 41. Although the reactions are contiguously conducted, there is sufficient spacing between the plasma flame 34 and the bed 41 of reactant particles 40, that the high temperature present in the flame does not melt the bed, making it impassable to the flow of gas. If the flame 34 were cool enough relative to the melting point of the reactant particles, this spacing would be unnecessary.

In accordance with the process of the present invention, the reactant particles are carbon and the co-reactant is metal fluoride and the desired product is tetrafluoroethylene (TFE).

The reactions occurring in the process of the present invention can be depicted as follows:

In the plasma:

(1) metal fluoride→metal+reactive fluorine

The reaction occuring with carbon can be depicted as follows:

(2) metal+reactive fluorine+C→metal+$CF_2$: The formation of $CF_2$: is presumed because of the subsequent formation of TFE when the carbon reaction mixture is quenched. The presence of excess C drives the reaction towards the production of $CF_2$: rather than allowing the fluorine to react with the metal to reform metal fluoride or to form $CF_4$.

The quench reaction can be depicted as (3) $2CF_2: \rightarrow CF_2=CF_2$

In operation using these starting materials, the metal fluoride is fed to the reaction chamber 10 either via space 26 between the electrodes or via line 42, in which case another gas is fed through space 26. In either case, the metal fluoride is subjected to the plasma, formed from itself alone or in conjunction with the other gas. The plasma flame represents a large volume of plasma. The result is dissociation of the metal fluoride into metal and reactive fluorine present as a gaseous mixture. This gaseous mixture is the flow of gas at this point of the reaction as referred to above.

This gaseous mixture being directed at the bed 41 of carbon particles by the gas flow within the reaction chamber 10, flows in intimate contact with the carbon particles to react with them. The heat and energy from the plasma is thus available for driving the reaction between the reactive fluorine in the gaseous mixture from the plasma and the carbon particles 40 but the temperature is not as high as to cause bulk melting of these particles, which would occur at temperatures above 3550° C. There may be a heat of reaction of the fluorine and carbon which would raise the bed temperature, but the process conditions should be controlled to keep the bulk bed temperature below 3550° C. There may be some incidental melting or even vaporization of the carbon particles closest to the plasma flame, which will be consumed by reaction with the reactive fluorine. While the plasma such as plasma flame 34 may be at temperatures of higher than the bed 41 such as at least 4500° C., wall cooling and other cooling, the bed of carbon particles and the feed of carbon particles drop the gas temperature rapidly to a temperature of no greater than about 3500° C. If the heat from the plasma flame is insufficient to provide the desired temperature needed for the reaction between reactive fluorine and carbon, then external heating and/or heating of the feed of carbon particles can be utilized.

The result of the reaction between solid carbon and fluorine is the formation of gaseous precursor to TFE, (equation (2)) and the TFE is formed by quenching within quenching chamber 44 (equation (3)) and recovery therefrom via outlet line 48 as shown in the Figure. The quenching causes the gaseous metal to condense, usually to a solid for easy separation from the still gaseous TFE. Preferably, the temperature of the wall of the reaction chamber 10 in the region of the carbon bed 41 is above the boiling point of the metal and undissociated metal fluoride, so that any solidification is delayed until quenching in chamber 44.

The process of the present invention provides the following advantages: The metal fluoride starting material can be inexpensive, especially relative to the cost of HCFC-22 which is often the feed source for fluoroolefins. A single plant can be used with relatively low investment. No HCl is produced in the process of the present invention, which simplifies the refinement of the TFE and avoids the need of disposal of the HCl or its further processing for recovery. The desired TFE and other valuable perfuorocarbons can be produced in high yield. The metal of the metal fluoride can be recovered, whereby its value further contributes to the economy of the process of the present invention.

Further details of the process and apparatus will be described hereinafter.

The reaction between metal fluoride and carbon first involves the removal of the fluorine atoms from the metal fluoride, i.e., its dissociation. Thermodynamically, as an equilibrium reaction, the reformation of the metal fluoride is to be expected. To make the dissociation reaction occur, the reactants are exposed to sufficient energy which is effective to energize the feed material, i.e., to cause dissociation of at least a portion of the metal fluoride reactant. This dissociation can be into radicals, atoms, and/or ions, which in essence is the excited state for the feed material. In a sense, the reaction is being initiated by dissociation energy being present in the reaction chamber. The plasma is the embodiment of this dissociation energy. The metal fluoride is excited to the point that the fluorine from the metal fluoride feed is free to combine with the carbon in the subsequent reaction outside of the plasma flame.

The plasma is an energized form of the feed material, whether the plasma is formed from the metal fluoride or is formed from a gas other than the metal fluoride, in which case the metal fluoride also becomes energized when fed into the plasma flame.

The feed material can also contain another reactant, as in the case of CO as a gaseous feed to the arc or to the plasma created by a relatively inert gas, such as argon. At the high temperature of the plasma, the identity of the reaction product is essentially unknown, although it is believed to be the precursor to carbonyl fluoride ($COF_2$), by virtue of this being the product obtained in the gaseous reaction mixture if the plasma were quenched. Reaction of the gaseous precursor to $COF_2$, which can also be referred to as an F/CO combination with carbon, forms the gaseous precursor to tetrafluoroethylene, which upon quenching, yields TFE. In this embodiment, the reaction occurring in the plasma is believed to be as follows:

(4) 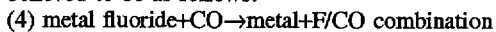

When the gaseous reaction mixture is then brought into contact with the bed of carbon particles such as shown in the Figure, the reaction can be depicted as follows:

(4) 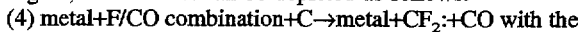

$CF_2$: precursor upon quenching becoming perfluoroolefin, primarily TFE. The CO formed in this reaction can be recycled to form the CO feed to the plasma or to form the plasma.

The tendency of the dissociated fluorine and metal in the plasma to recombine can be minimized or avoided by rapidly using up the active fluorine, whether it is by itself or associated with another co-reactant such as CO, and this is accomplished in the process and apparatus described above by conducting the subsequent reaction with carbon at a site which is contiguous with the plasma. Thus, the reaction with carbon is almost immediate after the metal fluoride has become dissociated. The plasma temperature will usually be higher than the temperature of the reaction with carbon. In this case, the cooling of the gaseous mixture exiting the plasma, and upon contacting the carbon particles, tends to inhibit the reactive fluorine from recombining with the metal. The presence of gas other than vaporized or gaseous metal fluoride, (e.g., a non-reactive or inert gas fed through the arc 30 via space 26 between the electrodes, to form the plasma) is preferred because this retards the recombination of the reactive fluorine with the metal, thereby enhancing the availability of the reactive fluorine for reaction with carbon in the carbon bed 41, to form desired TFE precursor. Such gas serves as a carrier for the metal fluoride which dissociates to become part of the plasma, together forming the gaseous reaction mixture which next contacts the carbon bed 41.

The apparatus of the present invention provides an economical chemical reactor for realizing these process advantages.

With respect to the starting materials of the process of the present invention, carbon can be obtained commercially from a wide variety of sources. Clearly, the purer the carbon, the fewer the by-products in the process. Water, as much as possible, should also be excluded from the carbon and the source of metal fluoride. Extraneous water allows the formation of HF and metal oxides. It is also preferred that the carbon be deoxygenated so as to not provide oxygen to the reaction system. Exclusion of oxygen from the reaction system avoids the formation of metal oxide byproducts and oxygen-containing fluorocarbons.

The metal fluoride can be a compound or mixture of compounds, each of which contains one or more fluorine atoms. It is the fluorine atoms that are the active reactant portion of the metal fluoride, so the metal portion thereof can have a wide range of identities. Examples of metals (as fluoride), or mixtures thereof include lithium, sodium, potassium, magnesium, calcium, chromium, manganese, iron, nickel, copper, zinc, aluminum, boron, and silicon. The preferred metals come from Groups IA, excluding hydrogen, IB, IIA, IIB, IIIA, IIIB, IVA, IVB, VB, VIB, VIIB, and VIII of the Periodic Table (R. H. Perry and C. H. Chilton, *Chemical Engineer's Handbook*, 5th Ed., McGraw-Hill, inside cover (1973)). The metal fluoride can be economically obtained from mining operations, and will be non-carbonaceous (contains no carbon). Metal fluorides used in the present invention are much more difficult to dissociate, and thus be reacted with carbon than fluorocarbons such as $CF_4$ and $C_2F_6$. Generally, the metal fluorides such as $CaF_2$ and silicon fluoride require at least 100% more energy to cause dissociation, which is difficult to achieve in the millesecond contact (exposure) time of the metal fluoride with the plasma flame. One of the reasons for the much greater energy required for dissociating metal fluoride is that a much greater number of chemical bonds need to be broken to make fluorine from metal fluoride available for reaction with carbon. The metal/fluoride bond for such metal fluorides as silicon fluoride, calcium fluoride, and sodium fluoride is also much stronger than the carbon/fluorine bond. In the case of fluorocarbons, some of the carbon/fluorine bonds are already formed, whereby fewer carbon/fluorine bonds need to be broken. Preferably, the metal portion of the metal fluoride has inertness or low reactivity to the carbon or carbon/fluorine moiety (reaction product) under conditions of the reaction.

Preferred metal fluorides include NaF, $CaF_2$ and silicon fluoride such as $SiF_4$, $Si_2F_6$ and metal silicon fluoride such as calcium fluorisilicate. Preferably, the metal fluoride does not contain any other halogen atoms. The presence of oxides in the metal fluoride is less desirable since the oxygen can form less desirable metal oxides including carbon/oxygen compounds.

The present invention having revealed the starting materials and reaction mechanism to be used, one skilled in the art will recognize many ways to subject metal fluoride to a plasma to generate the dissociation energy required. Thus, the reaction can be carried out by producing the dissociation energy by an electrical arc, either A.C. or D.C., using a plasma reactor, or by electromagnetic energy created for example by an induction coil or microwave, or by heating alone. In the case of the electrical arc, the applicator of the dissociation energy is within the reaction zone, as in the case of the Figure while in the case of the electromagnetic energy, the applicator of the energy, e.g., an induction coil, can be exterior to the reaction chamber, but creating the dissociation energy within the reaction chamber.

The plasma reactor is one type of apparatus for carrying the dissociation of the metal fluoride to prepare it for the reaction with carbon. The electrical discharge, e.g., arc 30, between these electrodes can be rotated by a coil-induced magnetic field or the arc can be stationary. The electrodes can be, among other materials, of copper and can be water cooled so as to provide long operating time. Preferably, the material of construction of the electrodes is such that the electrodes are not consumed by reaction with the metal fluoride feed. Thus, if the metal fluoride is fed into the plasma flame, i.e., downstream from the arc, carbon electrodes can be used. If the metal fluoride, however, is fed through the arc, then non-carbonaceous material is preferably used as the material of construction of the electrodes.

It is the region of the arc that provides the excitation energy useful in the present invention, which manifests itself as intense heat to produce a plasma of material fed to it. The plasma forms a visible glow region extending downstream from the arc, in the direction of the fluid flow within the reactor, which glow area is called the plasma flame, such as flame 34 in the Figure.

Measures can be taken, e.g., a rotating electric arc, to produce a turbulent mixing action in the plasma flame and if desired within the arc, to give high operating efficiency.

The gaseous feed material can be directly or indirectly energized, i.e., subjected to the dissociation energy generated by the rotating electric arc or by other means. An example of direct exposure would be when a reactant feed, such as $SiF_4$, is fed to the electrical arc (or the electromagnetic field of a different apparatus). An example of indirect exposure would be when a gaseous non-reactant is fed the arc (direct exposure), and the resultant excited or dissociated gas (plasma) is then brought into contact with the metal fluoride reactant (indirect exposure) in the plasma flame downstream from the arc. Another example of indirect exposure would be when a reactive gas such as CO is directly exposed to the arc or electromagnetic field to cause a portion of the CO to dissociate, and the energized CO is then brought into contact with the metal fluoride reactant. In still another embodiment, the plasma is first formed from an inert or non-reactive gas, such as argon or helium and metal fluoride and possibly CO are then added to the plasma flame. The plasma flame is formed from the particular feed material, inert or non-reactive gas acting as a carrier and/or one or both reactants, that is directly exposed to the arc in the plasma reactor. Thus, the present invention includes all of these possibilities for subjecting feed materials to the dissociation energy (energizing of the feed materials) of the thermal plasma. These possibilities can be effective to prolong electrode life in the case when one or more of the feed materials are corrosive to the electrodes. When inert gas is fed to the arc to form the plasma flame and the metal fluoride is fed to the flame downstream from the arc, the amount of inert gas used is preferably an excess with respect to the amount of metal fluoride, so as to provide the energy (heat) needed to dissociate the metal fluoride. Preheating of the metal fluoride enables the amount of inert gas to be reduced. In general, however, at least 5 moles of inert gas/mole of metal fluoride will be used, and excesses such as at least 10 or 20 moles of inert gas/mole of metal fluoride can be used. In another embodiment of apparatus useful in the present invention, the plasma can be created between an electrode and an oppositely charged electrode in or near a bed of carbon particles, in what is commonly known as a transfer arc process. In this embodiment, the metal fluoride is first dissociated, to form gaseous metal and reactive fluorine, to form the plasma which envelopes the transfer arc, and these gaseous materials are flowed into and through the bed of carbon particles to form TFE precursor, i.e., the reaction between reactive fluorine and carbon occurs primarily in the bed of carbon particles.

The energy used to energize or excite the feed material to form the thermal plasma can generally be quantified by specification of the power input to create the plasma plus the thermal energy available if any of the feed materials to the reaction zone are preheated.

The temperature produced by the arc can be controlled by varying the arc power input and/or the feed rate of material through the arc. For the particular power available from the reactor, the flow rate of the feed material is adjusted so that the feed material becomes energized (excited) by this exposure to dissociation energy and becomes part of the plasma. Control of power input and feed rate will also determine the temperature of the plasma created by other electrical means. Thus, the temperature of contact between the gaseous mixture and the carbon can be controlled. The preferred temperature of the carbon bed 41 is from 2800° C. to 3500° C. at atmospheric pressure. Fluorine is most tightly bound to such metals as silicon, magnesium, calcium, and aluminum, and less so to metals such as iron, copper, and zinc. In general, less energy (lower temperature) is required to dissociate the metal fluoride when the metal/fluorine bond is weaker. For any particular metal fluoride, lower pressure within the reaction zone, allows the dissociation to occur at lower the temperature. The pressure can be sub-atmospheric, such as at least 20 mm Hg and preferably at least 300 mm Hg, atmospheric, or super-atmospheric. By way of example of the effect of pressure, if carbon tetrafluoride were fed to the plasma, the level of dissociation at atmospheric pressure and 2700° C. would be similar to that obtained at 10 mm Hg and 2200° C. Above about 2800° C., and at atmospheric pressure and equilibrium, $CF_4$ is totally dissociated into $CF_2$: radicals, fluorine, and other carbon and carbon/fluorine related species. It is because of this dissociation and incumbent formation of $CF_2$: radicals that rapid quenching bypasses the reformation of $CF_4$ and other related saturated perfluorocarbons, leading to principally the formation of perfluoroolefins, primarily TFE.

For the range of fluoride starting materials that can be used, along with the range of pressures that can be used, it is believed that the heat present in the creation of the dissociation energy (plasma), the temperature will be at least 1500° C. at atmospheric pressure. More often, the temperature will be at least 3500° C. and preferably at least 4500° C. at atmospheric pressure. Extremely higher temperatures may be used, e.g., even more than 10,000° C. At such temperatures, the metal fluoride, if not gaseous at ambient temperature, is either completely or partially volatilized in the plasma. Silicon tetrafluoride is gaseous at ambient conditions and thus provides a convenient feed to the reaction zone. $CaF_2$, e.g., boils at 2500° C. and can, therefore, be present as a gas or mixture of gas and liquid in the reaction zone, depending on the temperature and pressure in this zone. The metal fluoride may thus be present as a mixture of gas and liquid material, again depending on the particular fluoride compound and reaction conditions. Temperatures of about 2000° C. and less can conveniently be measured with a thermocouple. Higher temperatures, especially those of an electrical arc or plasma flame can be determined by known means, usually estimated by mathematical analysis of the power inputs, feed compositions and flow rates.

The proportion of particulate carbon at which the gaseous reaction mixture from the plasma is directed is preferably sufficient to combine with the fluorine atoms of the metal fluoride so that fluorine atoms are not left over to recombine with the metal to re-form metal fluoride. This is not to say that all of the metal fluoride feed to the reaction zone will react with the carbon in a single pass through this zone. It may be desirable to react only a portion of the metal fluoride in a single pass through the zone and to recycle unreacted metal fluoride to the reaction zone for further conversion. Preferably, however, the reaction is conducted so that a single pass is sufficient, wherein at least 50% of the metal fluoride is stripped of its fluorine and more preferably, at least 85%, and even more preferably, at least 90%.

The availability of excess carbon leads to the preferred collision of free (reactive) fluorine with the carbon to form the TFE precursor which is believed to be $CF_2$: radicals, which with further quenching forms TFE. The efficiency of the carbon in this regard is enhanced by the high surface area presented to the free fluorine by the particulate shape of the carbon and by the carbon particles being porous. Though there is usually a great excess of carbon, the metal from the metal fluoride is generally much less reactive with the carbon, especially if the reaction temperature above the perforated plate 20, i.e., the carbon reaction zone, is kept above the temperature at which the metal either condenses or reacts with carbon to form metal carbide, e.g., at least 1500° C. or at least 2000° C. (atmospheric pressure) depending on the temperature at which the particular gaseous metal condenses. Subsequent quenching of the fluorine/carbon gaseous reaction mixture causes the metal to condense, i.e., liquify or solidify, so that it is in a less reactive state. The large excess of carbon in bed 41 that can be present, can be at least 20 atoms of carbon/two fluorine atoms and preferably, at least 100 atoms of carbon/two fluorine atoms.

The resultant gaseous reaction mixture is cooled rapidly to a temperature less than 500° C., to obtain TFE, and relatively small amounts of higher perfluoroolefins, notably hexafluoropropylene (HFP) and desirable saturated perfluorocarbon such as hexafluoroethane. TFE is the preferred reaction product and is preferably present to constitute at least 60 wt % of the perfluorocarbon obtained from the converted metal fluoride, more preferably at least 80 wt % thereof and even more preferably at least 90 wt %. The rapid cooling (quenching) is preferably carried out at a rate greater than 10000° C./sec.

When the metal fluoride is silicon fluoride, the silicon recovered, e.g., from the quenching chamber 44 shown in the Figure, can be of good purity, making this a valuable byproduct of the process of the present invention although further purification may be desirable for specific applications. Recovery of silicon can be enhanced by the quench particles 45 therein being cooled silicon particles. The silicon from the reaction condenses on these particles, increasing their particle size, but without causing the silicon particles to stick together because of the rapid quenching of the Si through any liquid state. The resultant larger silicon particles are removed from the chamber 44 by auger 46 for cooling and recycling to the chamber for additional silicon growth. As the silicon particles grow too large, they can be removed by screening during the recycling step and collected in receptacle 52, and small particles of additional silicon added as make-up in the quenching chamber. When other metal fluorides are used, the quench particles can be of the same metal, whereby the condensed metal from the metal fluoride does not have to be separated from the quench particles.

In another embodiment, particles 45 of other solid materials, such as carbon, can be used in the quenching chamber, and the condensed metal product can then be separated by conventional means from such other solid material particles. The formation of metal carbides is minimized or avoided in the bed 41 of carbon particles by the short time of exposure and is avoided in the bed 47 of carbon particles by short exposure time and rapid quenching. Gases and/or liquids can also be used as part or all of the quenching medium.

The presence of any non-gaseous materials in the plasma will simply fall into and possibly through the bed of carbon particles and can be collected in the auger 46 if they pass through the bed. The same is true for any carbon particles which pass through the holes in perforated plate 20. As reference points, the boiling point of carbon is 4827° C., silicon is about 2350° C., calcium is 1480° C., calcium fluoride is 2500° C., silicon tetrafluoride is −86° C., and silicon dioxide is 2330° C. Melting points of these materials are as follows: carbon about 3550° C., silicon 1410° C., calcium 840° C., calcium fluoride 1420° C., silicon tetrafluoride, −90° C. and silicon dioxide 1720° C.

The desired perfluoroolefins and saturated fluorocarbons are separated from the reaction product by any variety of methods known to those skilled in the art, including distillation, adsorption, or absorption. Undesired fluorocarbons, any unconverted metal fluorides and any undesired perfluoroolefins can be recycled to the plasma or simply into the reaction zone, such as inlet line 50 in advance of the reaction with carbon. For example, when $CF_4$ is produced as a byproduct of the process, this fluorocarbon can be recycled to the plasma flame via line 50. Usually, the amount of $CF_4$ present in the fluorine/carbon reaction mixture after quenching will be less than 40 wt % based on the total weight of fluorocarbon present, more preferably less than 20 wt % and even more preferably, less than 10 wt %.

EXAMPLE 1

This example illustrates the synthesis of tetrafluoroethylene from silicon tetrafluoride using small scale plasma equipment. The plasma-generating equipment is a Metco (Model MBN) unit and the plasma torch is mounted across the top opening of a water-cooled copper cylinder forming a plasma reactor having an inner diameter of 5.72 cm and a length of 15.24 cm. The pressure within the reactor is maintained at 25 torr using a downstream vacuum pump. The outlet end of the reactor communicates with a water-cooled heat exchanger. The plasma carrier gas consists of argon feed to the torch at a flow rate of 7.5 liters/min (STP). The plasma power supply operates at a current of 500 amps and a voltage of 22 volts, producing a power input of 11.0 KW. The argon plasma flame extends into the copper reactor via the inlet end of the reactor, and energy balance calculations indicate the temperature of the argon plasma flame (bulk gas temperature) at the inlet to the reactor is in excess of 10,000° C.

Silicon tetrafluoride is injected at a rate of 0.2 liters/min (STP) perpendicular to the argon plasma flame using two injection nozzles mounted in the reactor wall ¼-inch (6.35 mm) below the plasma torch exit. The injection nozzles are sized with a diameter of 2 mil (0.05 mm) to promote sonic velocities and good mixing of the $SiF_4$ in the plasma flame, thereby promoting dissociation of the $SiF_4$ and formation of free fluorine. A fixed-bed of granular carbon is situated ½ inch below the plasma torch exit and in the plasma reactor to provide elemental carbon for reaction of $SiF_4$ to tetrafluoroethylene and other fluorocarbons. The carbon is an activated form of carbon obtained from Aesar and in the form of 3×6 mm extruded pellets. The total weight of granular carbon loaded in the reactor is 27 grams to form a fixed-bed of carbon pellets with a thickness of 2.5 cm. The carbon bed is supported by a graphite support plate which has holes bored into it to allow the reactor gas to pass through without appreciable pressure drop, e.g. less than 10 TORR but small enough to retain the carbon pellets.

The $SiF_4$ is at room temperature when injected into the plasma flame and is rapidly heated by efficient contact and mixing with the argon plasma flame. The resulting hot gas mixture passes through the bed of granular carbon while still at very high temperatures. The gaseous reaction product stream is then cooled by contact with cooled reactor walls downstream, and further quenched to ambient temperature by passing the product gas through a water-cooled heat exchanger. Samples of the product gas are collected in bags of TEDLAR® polyvinyl fluoride film for infrared analysis. Conversion of $SiF_4$ to fluorocarbon is measured at 19%. Spectroscopic analysis of the mole percentages of fluorocarbon products is 68 mole % tetrafluoroethylene ($C_2F_4$), 17 mole % carbon tetrafluoride ($CF_4$), 10 mole % hexafluoroethane ($C_2F_6$), along with trace levels of carbonyl fluoride (2 mole %, $COF_2$) and trifluoromethane (3 mole %, $CHF_3$). The oxygen and hydrogen present in these reaction products are believed to come from the granular carbon reactant. The conversion of $SiF_4$ and yield of TFE can be increased by recycling unreacted $SiF_4$ and the $CF_4$ and $C_2F_6$ reaction products to the plasma flame. Following the run, the weight of carbon remaining is 14.4 g, indicating that 46.5% of the carbon has been vaporized and/or converted to fluorocarbons.

EXAMPLE 2

In this Example, the desired reaction is as follows:

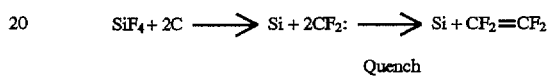

Quench

The equipment used in this Example is similar to that in the Figure and is larger than the equipment described in Example 1. The feed rates for this example are given in the Table below. Five mols of argon are fed to the plasma gun (between the oppositely charged electrodes) for each mol of silicon tetrafluoride fed into the resulting plasma flame and the arc is magnetically rotated. Thus, 200 grams/minute of argon are fed through the electrodes of the plasma gun at atmospheric pressure, and 104 grams/minute of preheated silicon tetrafluoride are fed into the flame, resulting in a combined temperature in the range of 6500° C. Carbon pellets (6.4 mm in length and diameter) are fed to the carbon bed at the rate of 24 grams/minute. The carbon bed contains 480 grams of pellets on startup, thus providing a large excess of carbon for the reaction with the hot gaseous plasma. The heat losses through the walls of the reactor and from the added carbon produce a temperature in the range of 3400° C. at the surface of the carbon bed pellets. As the gases progress through the carbon bed, additional heat losses reduce the temperature to about 2700° C. as they exit the support plate into the quench chamber. The gases are quenched by contacting with −100+200 mesh silicon particles which are at 30° C. These solid particles are sprayed upwards through a spouted tube into the hot gases exiting the carbon bed at a rate of about 2600 grams/minute and results in an exit temperature of the gases and solids of about 325° C. The exiting gases are further cooled for analysis and a portion of the gases are recycled on a continuous basis to assist in the spraying of quenching silicon particles. The solid particles are removed continuously from the bottom of the quench chamber, further cooled, and then recycled for additional quenching of the exiting gases. Analysis of the weight gain in the amount of quenching material shows that about 27.9 grams/minute are being added to this quench material. The composition of the condensed and solidified products is shown below. The overall material balance shows that during the run, excess carbon is being added to the bed at the rate of 1.9 grams/minute. To keep the bed from filling up, the carbon feed rate would have to be reduced to 22.1 grams/minute. For the more than 94% $SiF_4$ converted, the fluorine material balance shows that 98% ended up as fluorocarbons, with 85% being tetrafluoroethylene (TFE). If only TFE were desired, the other fluorocarbons could be separated and recycled back to the plasma process for conversion to TFE.

The unconverted $SiF_4$ could also be separated and fed back to the plasma process.

All values in the Table below are shown in grams/minute. The material shown as SiF is complexed with the silicon metal. Since silicon particles are used for quenching, a sample of the total quench bed solids is taken for analysis of the solids. The analysis below, made by material balance, does not show the amount of silicon from the quenching particles.

For solid analysis, small amounts of water are slowly added to a weighed sample, taken under nitrogen, of residual solids to remove the SiF complex which goes into solution. After washing to remove all of the SiF complex, the sample is vacuum dried and re-weighed to determine the amount of weight loss to be reported as the SiF complex. The residual dried sample is placed in a reaction tube inside a furnace and is heated, under vacuum, with a low flow of oxygen to look for and burn off any carbon, and in this example, none is found. The temperature is kept below 600° C. to minimize reaction with the silicon metal, which is then determined by difference after reweighing the cooled sample.

The total volume of the exit gases are monitored through a flow meter. The volume amount of $SiF_4$ in the exit gases is determined by double scrubbing a known volume of the exit gas in water, thus removing the $SiF_4$ by the reaction:

$$3\ SiF_4 + 2\ H_2O \rightarrow 2\ H_2SiF_6\text{(in water solution)} + SiO_2$$

The $SiO_2$ precipitates and stays with the water solution. The decrease in volume shows the amount of $SiF_4$ in the sample. After drying the residual exit gas, from the sample, over calcium sulfate, the remaining gas is analyzed on a gas chromatograph. A Hewlett-Packard 5880A series gas chromatograph is used for this analysis. A 20 foot long, ⅛th inch diameter, stainless steel column (from Supelco, Inc.), packed with 60/80 mesh Carbopack@ B, with 1% SP-1000, a high boiling liquid, is used to separate the individual components as shown in the analysis for the example. After a sample is injected into the gas chromatograph, the temperature on the column is held constant for 5 minutes at 40° C. and then the temperature is increased to 180° C., at a rate if 20° C./min. The area percents obtained from the thermal conductivity detector of the gas chromatograph are converted into weights and weight percents.

| Component | Feed Materials g/m | Product Streams g/m |
|---|---|---|
| Argon | 200 | 200.0 |
| $SiF_4$ | 104 | 6.0 |
| Carbon | 24 | 0.0 |
| SiF | — | 2.0 |
| Silicon | — | 25.9 |
| TFE | — | 81.3 |
| $CF_4$ | — | 5.7 |
| $C_2F_6$ | — | 2.5 |
| $C_3F_6$ | — | 1.8 |
| Misc. | — | 0.9 |
| Totals | 328 | 326.1 |

EXAMPLE 3

The equipment for this example is similar to that used in Example 2. The desired reaction sequence for this Example is as follows:

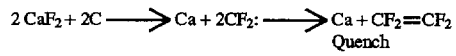
Quench

The feed rates and results are given in Table below. Ten mols of helium are fed to the plasma gun for each mol of preheated calcium fluoride injected into the flame, all at atmospheric pressure. The resulting combined temperature is in the range of 7500° C. Carbon particles, −4+5 mesh, are fed at 12 grams/minute to a 480 gram bed of similar carbon particles, thus providing an even larger ratio of carbon to fluorine than in Example 2. As with Example 2, heat losses to the carbon and through the reactor walls reduces the temperature to about 3200° C. at the surface of the carbon particles. Additional heat losses drop the temperature of the gases exiting into the quench chamber to 2800° C. In this Example, the gases are quenched by a stream of cooled −35+150 mesh carbon particles, again being fed from a spouted tube. The calcium and calcium fluoride condenses and solidifies on the carbon particles, but during the 20 minute length of the run do not appear to effect the performance of the quench process. Recovery of the metallic materials require separation from the carbon. The bed of carbon particles, and any adhering calcium or calcium fluoride, are circulated at about 1100 grams/minute, again using cooled recycled product gas to assist in the quenching and to convey the particles. The bulk temperature of the materials leaving the quench chamber is less than 300° C. Both the uncondensed exit gases and the solid particles are further cooled after being removed from the quench chamber. Analysis shows that the spray particles are gaining 43.4 grams/minute during the test run. In this Example also, the carbon feed rate would have to be reduced from 12 grams/minute to 10.5 grams/minute in order not to overfill the carbon bed in the carbon reaction zone. From the Table below, almost 90% of the calcium fluoride is converted and of the converted material, 90% goes to TFE. Since a fixed amount of carbon particles is used as the quench medium in this example, the analysis results reported in the table below are shown on a carbon free basis. The solid products are determined by taking a weighed sample, under nitrogen, of the quenched solids and slowly adding water to it to react with the calcium to form calcium hydroxide and hydrogen. The volume of hydrogen is collected to determine the amount of free calcium in the sample. The water is drained from the solids sample and the damp solids are place in a weighed tube in a vacuum furnace. The furnace is slowly taken to 600° C. to drive off the reacted and residual water, thus leaving only CaO, $CaF_2$, and carbon. The tube is re-weighed and returned to the furnace where oxygen is used to slowly burn the carbon leaving only the $CaF_2$ and calcium oxide. Since the amount of free calcium is determined via the hydrogen generation, the amount of calcium fluoride in the sample can be determined on re-weighing.

All values in the Table are in grams/minute. The miscellaneous column includes all other fluorocarbons not reported elsewhere.

| Component | Feed Materials g/m | Product Streams g/m |
|---|---|---|
| Helium | 40 | 40.0 |
| $CaF_2$ | 78 | 7.0 |
| Carbon | 12 | — |
| Calcium | — | 36.4 |
| TFE | — | 40.5 |

-continued

| Component | Feed Materials g/m | Product Streams g/m |
|---|---|---|
| $CF_4$ | — | 2.0 |
| $C_2F_6$ | — | 1.2 |
| $C_3F_6$ | — | 0.9 |
| Misc. | — | 0.5 |
| Totals | 130 | 128.5 |

What is claimed is:

1. A process for the preparation of tetrafluoroethylene, comprising
   (a) subjecting non-carbonaceous metal fluoride to a plasma to cause the metal fluoride to dissociate into a gaseous mixture of metal and reactive fluorine in the absence of halogen other than said fluorine,
   (b) flowing the gaseous mixture into intimate contact with particulate carbon at a temperature which is greater than the temperature at which the metal in the gaseous mixture condenses, whereby said reactive fluorine and said carbon react with one another to form gaseous precursor to said tetrafluoroethylene, and
   (c) quenching said gaseous precursor to obtain gaseous tetrafluoroethylene.

2. The process of claim 1 wherein the temperature of said plasma is at least 3500° C.

3. The process of claim 1 wherein the temperature of said plasma is at least 4500° C.

4. The process of claim 1 wherein the gaseous precursor is present in a reaction mixture which contains said gaseous metal and this reaction mixture is quenched to less than 500° C. at a rate of at least 10,000° C./sec.

5. The process of claim 1 wherein the metal fluoride is a silicon fluoride.

6. The process of claim 1 wherein the metal fluoride is calcium fluoride.

7. The process of claim 1 wherein the metal fluoride is sodium fluoride.

8. The process of claim 1 wherein said gaseous metal is removed from the gaseous tetrafluoroethylene or its precursor as a liquid or as a solid.

9. The process of claim 8 wherein said metal is silicon, calcium, or sodium.

10. The process of claim 1 wherein at least twenty atoms of carbon is present for each two fluorine atoms provided by said metal fluoride.

11. The process of claim 1 wherein the plasma is formed from an inert gas and the plasma has a flame portion, and the metal fluoride is subjected to the plasma by feeding the metal fluoride into said flame.

12. The process of claim 1 wherein the yield of said tetrafluoroethylene is at least 60 wt %.

13. The process of claim 1 wherein unreacted metal fluoride and undesired perfluorocarbons are recycled.

14. The process of claim 11 wherein said inert gas is recovered for recycle.

15. The process of claim 1 and additionally, subjecting CO to said plasma to form a combination of said reactive fluorine with CO, wherein said carbon of step (b) subsequently reacts with said combination to form said precursor to tetrafluoroethylene and CO.

16. The process of claim 15 and additionally, recycling the CO obtained from the reaction of said carbon with said combination in said plasma.

17. The process of claim 1 wherein the temperature of the reaction between said carbon and said reactive fluorine is less than the temperature of said plasma.

18. The process of claim 17 wherein said temperature of said reaction is 1500° C. to 3500° C.

19. The process of claim 1 wherein said gaseous metal is present with said gaseous precursor as a reaction mixture during said quenching and said quenching is carried out by contacting cool particulate solids with said reaction mixture, whereby said gaseous metal condenses on said solids.

20. The process of claim 19 wherein said particulate solids are of metal, essentially the same as said gaseous metal, whereby said gaseous metal condenses on said particulate solids to form larger particles of said metal.

21. The process of claim 20, wherein said metal is silicon.

22. The process of claim 1 wherein said plasma is created by flowing a gas through an electric arc at a flow rate effective to extend said plasma from said arc.

23. The process of claim 22 wherein the subjecting step is carried out by feeding said metal fluoride into said extension of said plasma.

24. Process of claim 1 wherein said particulate carbon is in the form of a bed and said flowing of the gaseous mixture is through said bed, and additionally, replenishing said bed with particulate carbon as it is consumed by reaction with said reactive fluorine.

25. Process of claim 1 wherein said gaseous tetrafluoroethylene is obtained in a mixture with other gaseous material, and additionally, recovering said tetrafluoroethylene from said gaseous mixture and recycling at least a portion of the remainder of the gaseous mixture to either the subjecting step or the flowing step.

26. Process of claim 1 wherein said plasma is created in a transfer arc.

27. Process of claim 24 wherein said plasma is created in a transfer arc.

* * * * *